United States Patent [19]

Shakkottai et al.

[11] Patent Number: 5,002,894
[45] Date of Patent: Mar. 26, 1991

[54] METHOD FOR THE DETERMINATION OF LIGNIN CONTENT OF A SAMPLE BY FLASH PYROLYSIS IN AN ATMOSPHERE OF HYDROGEN OR HELIUM AND METHOD THEREFOR

[76] Inventors: Parthasarathy Shakkottai, 2622 Gardi St., Duarte, Calif. 91010; Eug Y. Kwack, 20946 E. Canyon Ridge Rd., Walnut, Calif. 91789; Daniel D. Lawson, 5542 Halifax Rd., Arcadia, Calif. 91006

[21] Appl. No.: 202,401

[22] Filed: Jun. 6, 1988

[51] Int. Cl.$^5$ ............................................. G01N 33/46
[52] U.S. Cl. ..................................... 436/128; 422/78; 422/89; 422/94; 73/23.1; 73/864.82
[58] Field of Search ............................ 422/78, 89, 94; 436/128; 73/23.1, 864.82

[56] References Cited

U.S. PATENT DOCUMENTS 3,955,924  5/1976  Northmore et al. .................. 422/79
4,159,894  7/1979  Hu ........................................ 422/78

OTHER PUBLICATIONS

Gardner et al., "The Pyrolytic Behavior of Selected Lignin Preparations", J. Wood Chem. Technol., L5Y1), 1985, pp. 85-110, (Abstract only).
Windig et al., "Biochemical Analysis of Wooded Wood Products by Pyrolysis-Mass Spectrometry and Multivariated Analysis", J. Appl. Pyrolysis, (6) (3), 1984, (Abstract only).
Obst, "Analytical Pyrolysis of Hardwood and Softwood Lignins and its use in Lignin-Type Determination of Hardwood Vessel Elements", J. of Wood Chemistry and Technology, 1983, (3) (4):377-397, (Abstract only).

Primary Examiner—Robert J. Warden
Assistant Examiner—Lyle Alfandary-Alexander

[57] ABSTRACT

The lignin content of wood, paper pulp or other material containing lignin (such as filter paper soaked in black liquor) is more readily determined by flash pyrolysis of the sample at approximately 550° C. in a reducing atmosphere of hydrogen or in an inert atmosphere of helium followed by a rapid analysis of the product gas by a mass spectrometer. The heated pyrolysis unit as fabricated comprises a small platinum cup welded to an electrically-heated stainless steel ribbon with control means for programmed short duration (1.5 sec, approximately) heating and means for continuous flow of hydrogen or helium. The pyrolysis products enter an electron-ionization mode mass spectrometer for spectral evaluation. Lignin content is obtained from certain ratios of integrated ion currents of many mass spectral lines, the ratios being linearly related to the Kappa number of Klason lignin.

1 Claim, 10 Drawing Sheets

METHOD FOR THE DETERMINATION OF LIGNIN CONTENT OF A SAMPLE BY FLASH PYROLYSIS IN AN ATMOSPHERE OF HYDROGEN OR HELIUM AND METHOD THEREFOR

This invention was made with Government Support under Contract No. DE-A105-84-CE40684 awarded by NASA. The Government has certain rights in this invention.

BACKGROUND OF THE INVENTION

1. Field of the Invention

The present invention is directed towards a system and method of deriving the lignin content of paper pulp or other lignocellulosic material by a rapid pyrolysis of a small sample (1 to 5 milligrams) at approximately 550° C. followed by a determination of mass spectra or chromatogram.

2. Description of the Prior Art

The lignin content of pulp is determined by a quantity known as the Kappa number which is the volume in millimeters of 0.1N potassium permanganate solution consumed by one gram of moisture-free pulp under conditions specified in the method recommended by the Technical Association of the Pulp and Paper Industry (TAPPI). The TAPPI Standard has the number T236 hm-85 and the latest version was issued in 1984 (ref. 1). The procedure consists of weighing an amount of specimen which will consume between 30 to 70% of permanganate, disintegration of sample in 500 mL of distilled water, transfer to a 2 L reaction beaker at 25°+0.2° C., stirring continuously, addition of 100+0.1 mL of potassium permanganate solution and 100 mL of 4N sulphuric acid into a 250 mL beaker, bringing the temperature to 25° C. and adding it to the disintegrated pulp, starting immediately a stop watch and bringing the solution to 1000+5 mL, allowing the reaction to proceed and then stopping it at the end of exactly 10 min by adding 20 mL of 1N potassium iodide. After mixing, a titration with 0.2N sodium thiosulphate is done to determine end point using a few drops of starch indicator. A blank determination using the same method is also done without pulp. From the measured weights and volumes of chemicals consumed, the Kappa number is determined by the formulas given by the TAPPI standard method. The method takes approximately 30 minutes.

Recently an on-line Kappa sensor based on selective absorption of ultraviolet light by lignin has been developed by the Swedish Paper Research Institute and is available commercially bearing the name STFI OPTI-Kappa (ref. 2). It is very expensive.

Direct mass-spectrometric studies of the pyrolysis of carbonaceous fuels have been studied by Robert Evans et al (ref. 3). Similar studies have been motivated by a desire to find the chemical structure of pyrolysis components from various fuels. Relative abundances of various products depend greatly on the conditions of pyrolysis and previous studies have not been aimed towards a quantitative determination of lignin. Indeed, there has been a general skepticism that pyrolysis could ever be made a process reproducible enough to be useful for quantitative evaluation of condensed media.

However, this disclosure will show that quantitative determinations of lignin content by pyrolysis is possible.

OBJECTS AND SUMMARY OF THE INVENTION

It is the primary object of the present invention to provide a system and method for obtaining the lignin content of a small sample of pulp, paper, lignocellulosic matter or other substance containing lignin such as black liquor.

Another object is to provide a system for quality control in paper mills.

Yet another object is to provide an on-line lignin sensor for control of digestion of wood by determining the lignin content of either the pulp or the black liquors drawn from several locations in the digesters.

These and other objects of the present invention are achieved by pyrolysis of a small sample (1 to 5 mg) in a reducing atmosphere of hydrogen or in an inert atmosphere of helium. The pyrolysis process is very short and is approximately of duration equal to 1.5 sec. The temperature is adjusted to be near 550° C., at which maximum evolution of products related to lignin occurs. The pyrolysis occurs in a small platinum cup welded to a stainless steel ribbon which is heated electrically for the chosen time interval. A conventional electron ionization made mass spectrometer or an ion trap detector or a gas chromatograph determines the relative distribution of various component in the gases evolved during pyrolysis. The lignin content is determined from the ratio of the sum of integrated ion currents due to several mass groups characteristic of lignin to the integrated total ion current over a range of masses containing products from both cellulose and lignin. Alternately the ratio of ion current from a single lignin peak to a single cellulose peak can also be used.

If $Q(a,b)$ represents the integrated ion current over the duration of a measurement scan containing particles from mass $a$ to $b$, the quantity that is linearly related to lignin when pyrolysis occurs in a hydrogen atmosphere is found to be $[Q(135, 139)+Q(148, 188)]/Q(120, 300)$. When pyrolysis occurs in helium, the characteristic Q ratio that is linearly related to lignin content is different and is found to be $Q(135, 139)/Q(125, 129)$. The above results were obtained in one embodiment of the instrument where an ion trap detector was used as the mass analyzer. If a gas chromatograph is used for gas analysis equivalent results involving the ratios of areas of selected peaks in the chromatogram would be obtained.

BRIEF DESCRIPTION OF DRAWINGS

A more complete appreciation of the invention and attendant advantages thereof will be more clearly understood by reference to the following drawings where in.

DESCRIPTION OF THE PREFERRED EMBODIMENTS

The lignin analyzer is an instrument that can be used to determine the lignin content of a small sample of pulp (1 to 5 mg). The instrument yields the Kappa number in approximately 3 minutes.

Operation of the Pyrolyzer

Figure 1:
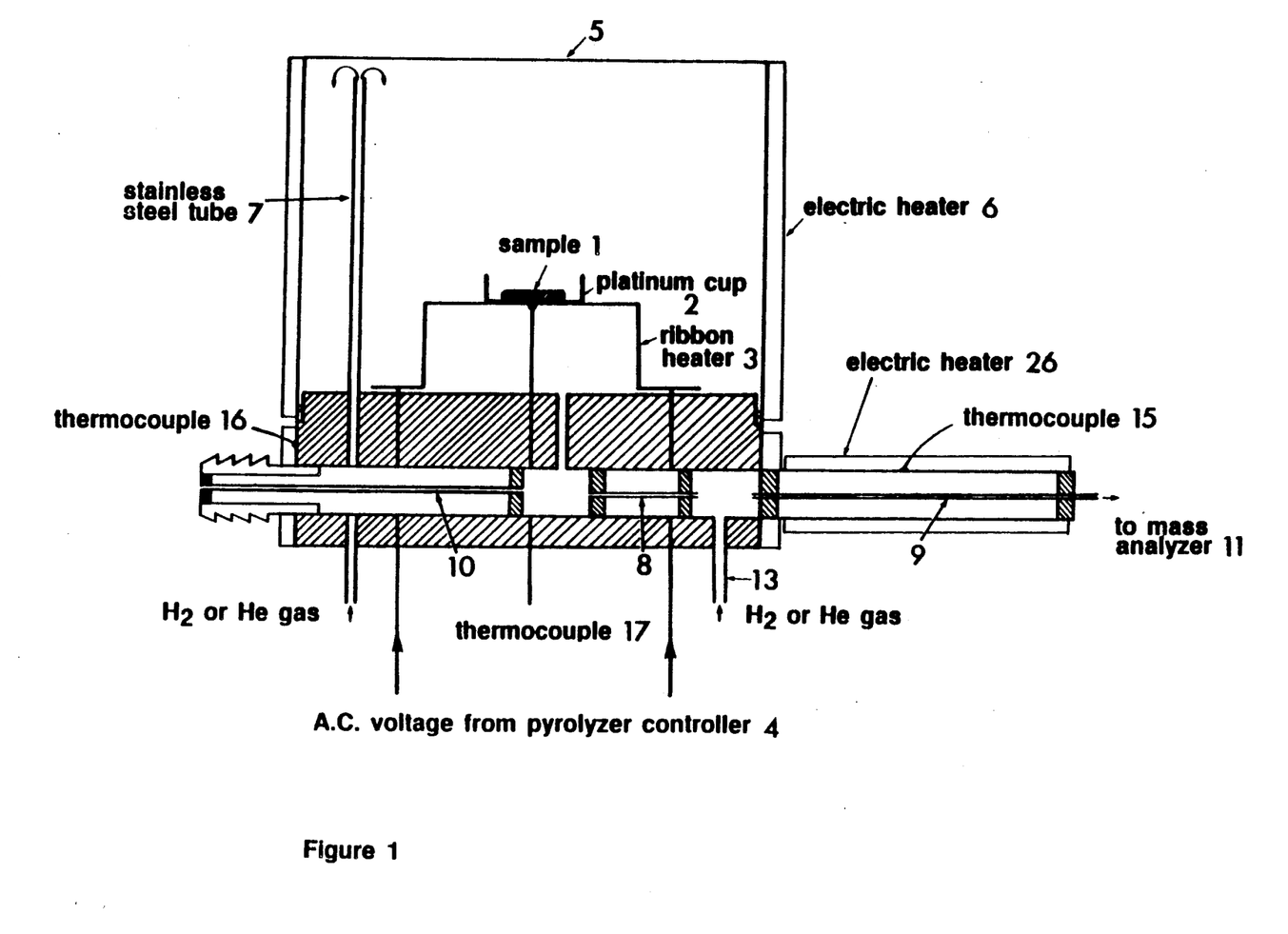
FIG. 1 is a sketch of the compact, continuous flow flash pyrolyzer showing the ribbon heated pyrolysis cup, entry tubes for hydrogen or helium and three capillary tubes for flow division.

As shown in FIG. 1, a small sample 1 of pulp is placed in the platinum cup 2 welded to a stainless steel ribbon 3 which is heated electrically by passing an a.c. current through the terminals 4. Pyrolysis takes place in an atmosphere of hydrogen or helium in the pyrolysis chamber 5 enclosing the sample 1. The chamber 5 is heated by an electrical heater 6. Hydrogen or helium enters the pyrolysis chamber 5 through a 1 mm bore stainless steel tube 7 at the top of the chamber such that it displaces air smoothly in approximately 30 seconds. This design prevents mixing with air which is detrimental to the operation of pyrolysis as well as to the operation of the mass analyzer which samples the pyrolysis gases. If air is present in the products of pyrolysis, the filaments of the mass spectrometer will be rapidly burned out.

The pyrolysis products present in chamber 5 are driven into the mass analyzer 11 through the capillaries 8 and 9. These products also escape to the ambient through a larger bore capillary 10. The capillary sizes are chosen such that only a small part of the flow goes into the mass analyzer 11. Typically, only a fraction 1/500 enters the mass analyzer 11. During data acquisition, the mass analyzer 11 scans repeatedly over a selected mass range and analyzes the gaseous products of pyrolysis. During this time (typically 60 sec), there is a gradual dilution of products of pyrolysis by hydrogen or helium which is continuosly mixing with the mixture of gases inside the chamber 5. This is in contrast to initial filling where hydrogen, being lighter than air, displaces air quickly without significant mixing.

Figure 2:
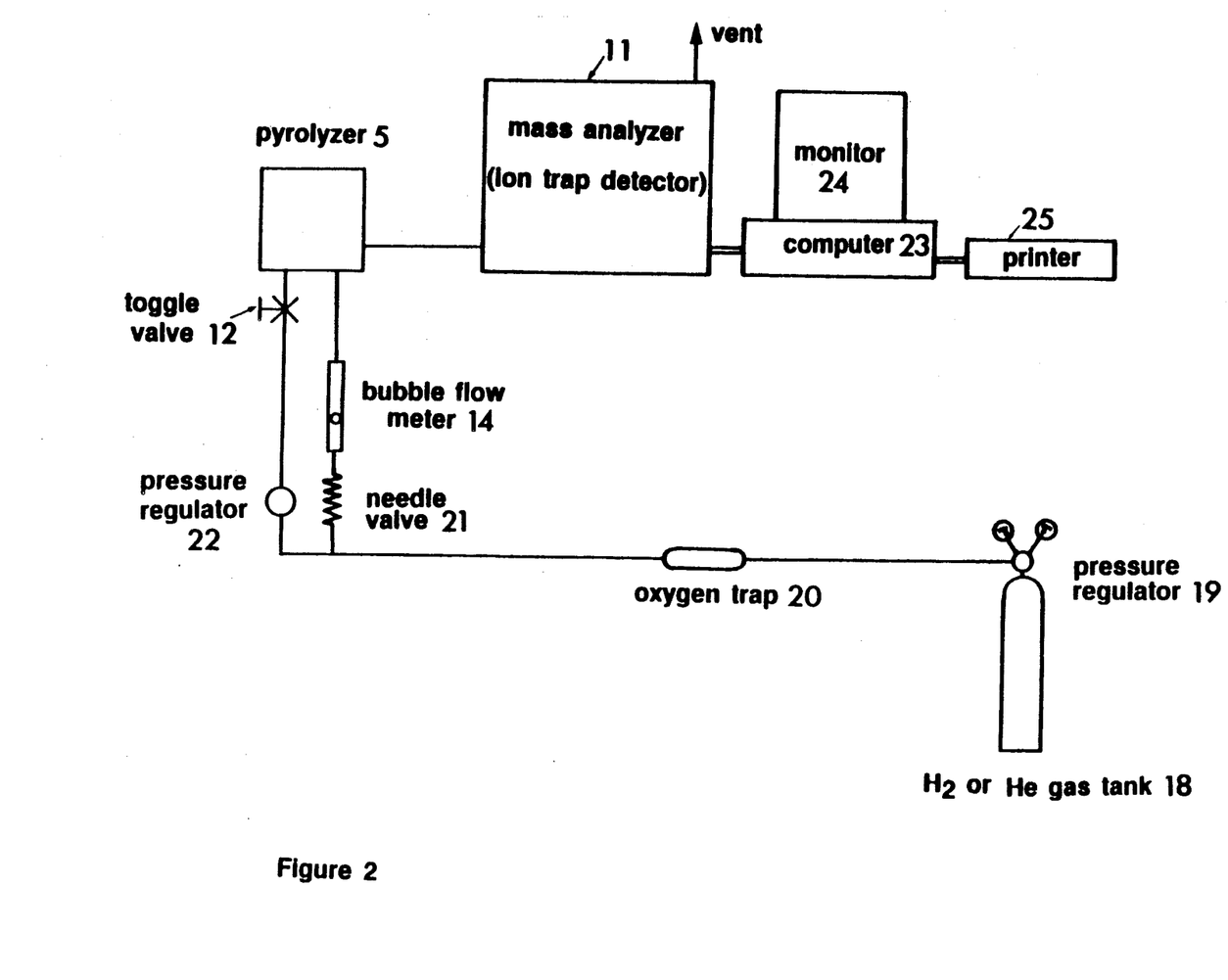
FIG. 2 is a schematic of the flow system including an oxygen trap, needle valve, bubble flow meter and a toggle valve to pressurize the pyrolyzer and displace air smoothly followed by a computer controlled mass analyzer, in one embodiment a commercially available ion trap detector.

After a sample scan (typically 60 sec), hydrogen or helium gas entry is stopped by closing the control valve 12 in FIG. 2. In the quiescent state, hydrogen continues to enter the mass analyzer 11 through the inlet tube 13. This flow is small and is typically 3 cc/min and is measured by the bubble flow meter 14 in FIG. 2. This flow divides in a different ratio by capillaries 8 and 10 on one side and capillary 9 on the other. Again, most of the flow goes to the ambient through Capillaries 8 and 10. This flow is led out of the room by a flexible plastic tube.

The rate of heating and cooling of the ribbon 3 is controlled by the duration and magnitude of the current through it. In this small continuous flow pyrolyzer, the pyrolysis profile is extremely reproducible. Thus, an important requirement for quantitative analysis is satisfied by proper flow design. Temperatures of the short transfer line 9, pyrolysis base and the platinum cup 2 are measured by thermocouples 15, 16 and 17 respectively.

In FIG. 2, the schematic diagram shows the gas flow line from the source of hydrogen or helium, gas tank 18, pressure regulator 19 which is set to approximately 40 psi, an oxygen trap 20 to remove residual oxygen from the gas, if any, providing a clean gas for pyrolysis. The same gas acts as a carrier to transport the products of pyrolysis into the mass analyzer. The needle valve 21 provide a high resistance to maintain a constant flow through the instrument. The bubble flow meter 14 is set to 3 cc/min in the quiescent state where toggle valve 12 is closed.

The pressure regulator 22 is set to 2 psi to operate the pyrolyzer when toggle valve 12 is open. After pyrolysis and gas sampling by the mass analyzer 11, the twist-lock lid of pyrolyzer 5 is opened and residues left in the cup removed. They could also be burned off by operating the ribbon heater once more in air. When the lid is open, air will not enter the mass analyzer because there will be a flow outwards from the inlet tube 13 through the capillary 8. The pressure at the inlet to capillary 9 is higher than atmospheric by approximately 0.5 psi.

The mass analyzer 11 analyzes the pyrolysis gas and this gas is vented to the atmosphere through one or more vacuum pumps in the instrument. One embodiment (shown here) is the use an ion trap detector 11 for mass analysis which has a turbomolecular pump and a fore pump in series to produce the required vacuum.

The computer 23, monitor 24 and printer 25 are used to control the mass analyzer 11, set up the proper parameters for acquisition, acquire data, store and process data, calculate Kappa numbers of the sample if it is a pulp, calculate the lignin content in terms of ratios if the sample is a liquid containing lignin such as black liquor. A simple way of measuring lignin content of black liquor is to soak a punched disk of filter paper (which is essentially only cellulose) in black liquor and use it for analysis. The mass peaks of cellulose in the fixed mass of filter paper provide an internal reference for evaluating lignin to cellulose ratios.

In FIG. 1, the transfer line 9 is heated by heater 26 to maintain a high temperature equal to 200° C. This prevents condensation of pyrolysis gases. The outer surfaces of heaters are insulated by wrapping with glass wool.

The Capillary Tubes

Tubing 9, 8 and 10 are made of stainless steel tubing of different bores. These are welded into sturdier larger diameter stainless steel tubing for ease of interfacing to other instruments such as mass spectrometers or gas chromatograph columns. Standard swage lock fittings can then be used for seals. The tubes are designed for easy disassembly and cleaning.

Quartz capillaries have also been used successfully. They are delicate, however, and sealing requires special graphite seals.

Summary of the Operation of the Ion Trap Detector

In one embodiment, the lignin analyzer uses a commercially available mass analyzer manufactured by Finnigan Mat. Detailed descriptions are given in the ITD operating manual.

Briefly it works like this. The sample and carrier gas ($H_2$ or He) enters the ion trap through capillary 9 into the ion trap where a low pressure equal to $1\mu$ Hg is maintained by a pumping system containing a turbo molecular pump in series with a fore pump. The ion trap operates well at such pressures because the neutral gas molecules provide a damping medium for the charged ions which oscillate in the cavity at its center.

Electron from a hot filament are pulsed into the cavity to ionize the gases by impact. Hydrogen is more efficient than helium and produces 3 to 4 times the number of ions compared to helium. A radio frequency field applied to ring electrodes sweeps away molecules of a certain mass depending on the frequency. As the frequency is swept, ions of gradually increasing masses are ejected and are detected by an electron multiplier detector. The ion current spectra are measured, stored and processed by the computer 23.

Data Acquisition

Data are acquired in the mass range 120 to 300 which contain two major peaks of cellulose. Typically, 60 scans are performed in 1 minute at 1 sec intervals. During each 1 sec intervals, the radio frequency voltage scans 8 times and average currents are stored. Normal operating voltage of the multiplier is 1400 volts.

Data acquisition is started first under computer control and after a few seconds, the pyrolyzer ribbon heater is turned on. This gives a clean baseline at the start of the pyrolysis profile of total ion current. Mass spectral data are stored in the computer and the scan stops after 1 minute. The pyrolyzer is opened and the residues removed from the platinum cup 2 as described earlier.

Experimental Data and Discussion

Figure 3:
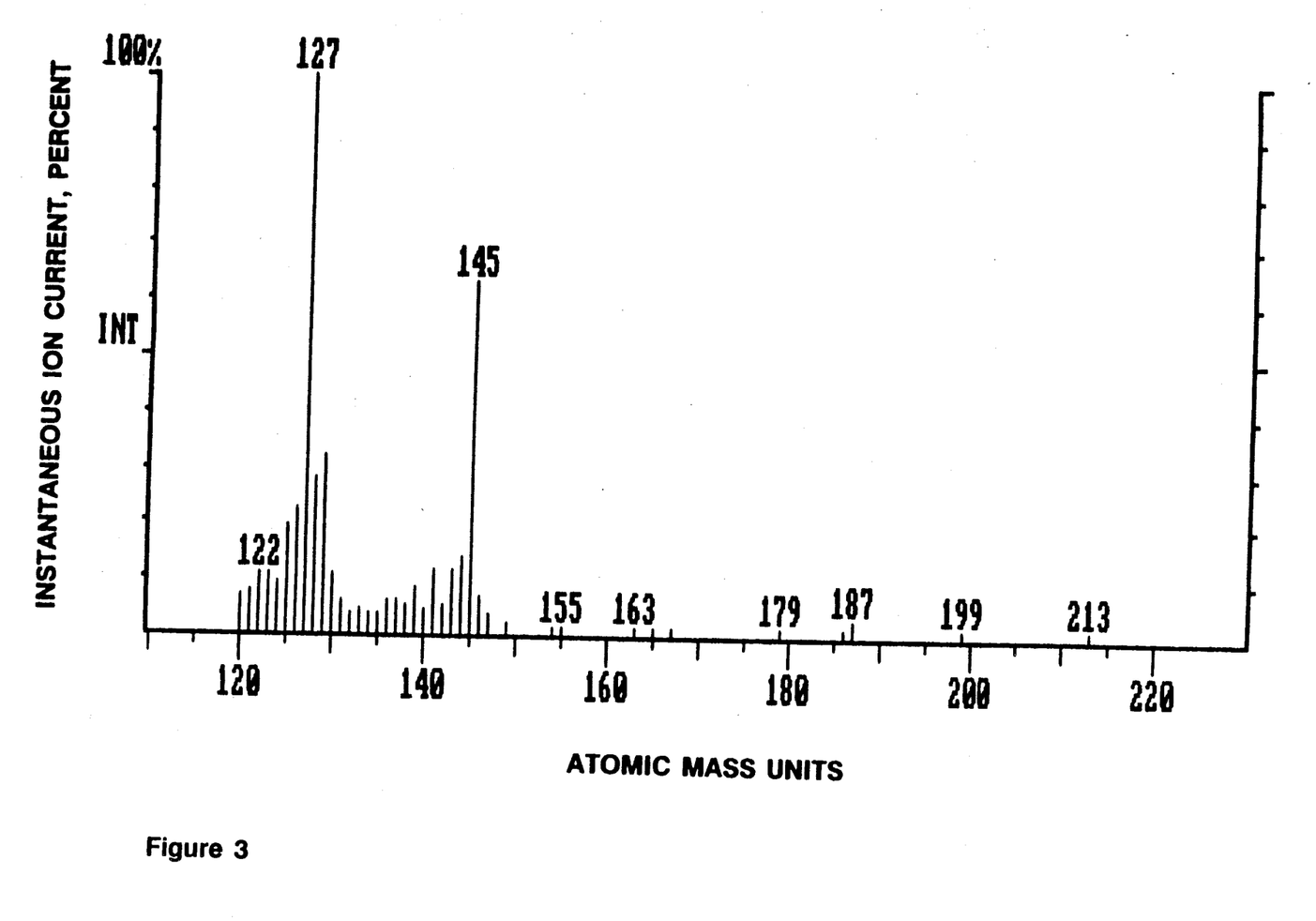
FIG. 3 is a record of the relative abundance mass spectrum at the peak of evolution of products from the pyrolysis in hydrogen of a 1 mg sample of filter paper where spectral lines at 127 and 145 atomic mass units, the lines from cellulose products, dominate.

First, the spectrum at the peak of evolution of products from the pyrolysis of a small sample of filter paper is considered in FIG. 3. This sample contains almost no lignin and therefore only the products from cellulose are present in the spectrum. The mass numbers 127 and 145 are the characteristic line of cellulose products in the displayed mass range. The ordinate is indicated as percent of full scale because the software adjusts the display such that the maximum in the spectrum is full scale. Here, the full scale represents 110,677 counts. Other setup parameters are also printed on such plots by the computer. These have been deliberately removed to present only the most important results. The ordinate INT stands for the instantaneous spectrum at a particular scan, in this case, scan number 9, at the peak of evolution.

Figure 4:
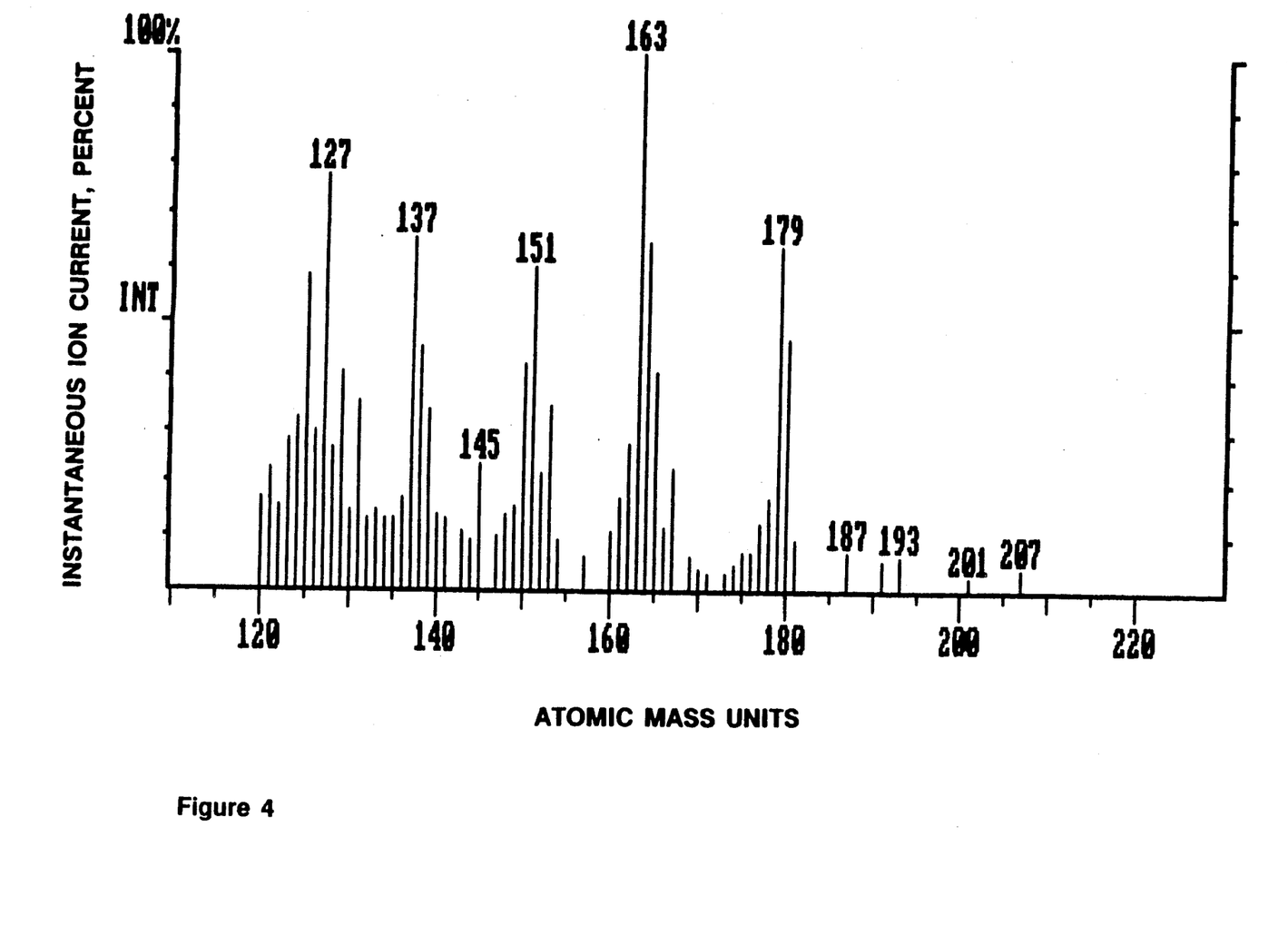
FIG. 4 is a record of the relative abundance of pyrolysis products from pine chips where strong spectral lines from lignin occur at 137, 151, 163, and 179 mass units, with each line accompanied by side bands, in addition to the lines at 127 and 145 atomic mass units from cellulose.

A spectrum at the peak of evolution from the pyrolysis of pine chips is shown in FIG. 4. In addition to the peaks 127 and 145 from cellulose, peaks at 137, 151, 163, 179 from lignin are also seen. The strongest peak occurs at 163 and 100% represent 40,317 ion counts detected by the multiplier.

Figure 5:
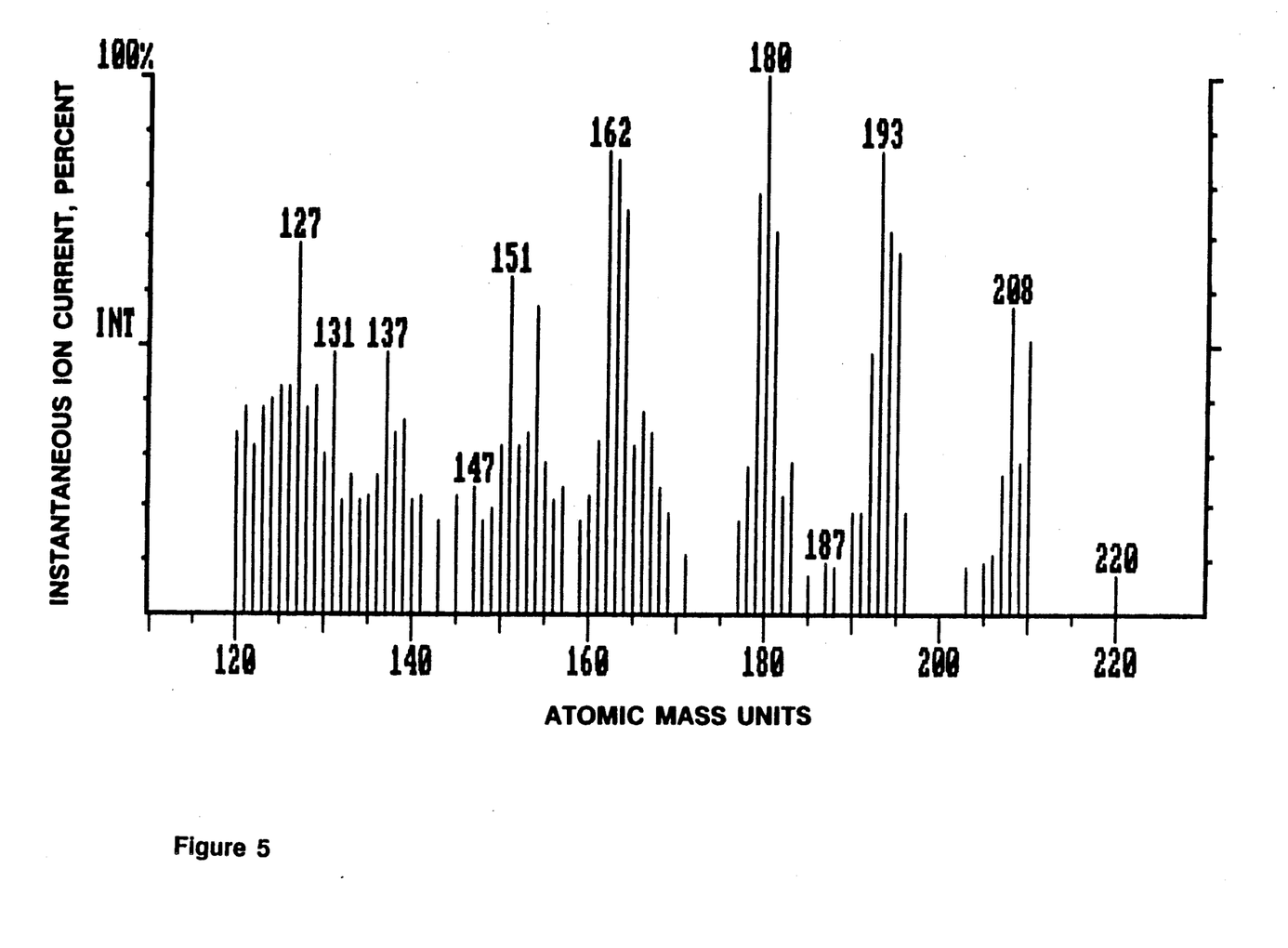
FIG. 5 is a record of the relative abundance of pyrolysis products from red oak chips where strong additional peaks at 193, 208 occur.

Lignin in hard woods produces additional products. A sample spectrum at the peak of evolution from the pyrolysis of red oak chips is shown in FIG. 5. Additional strong peaks of lignin at 193 and 208 are also observed. In this figure, the full scale on the ordinate is equal to 30,311 counts.

Figure 6:
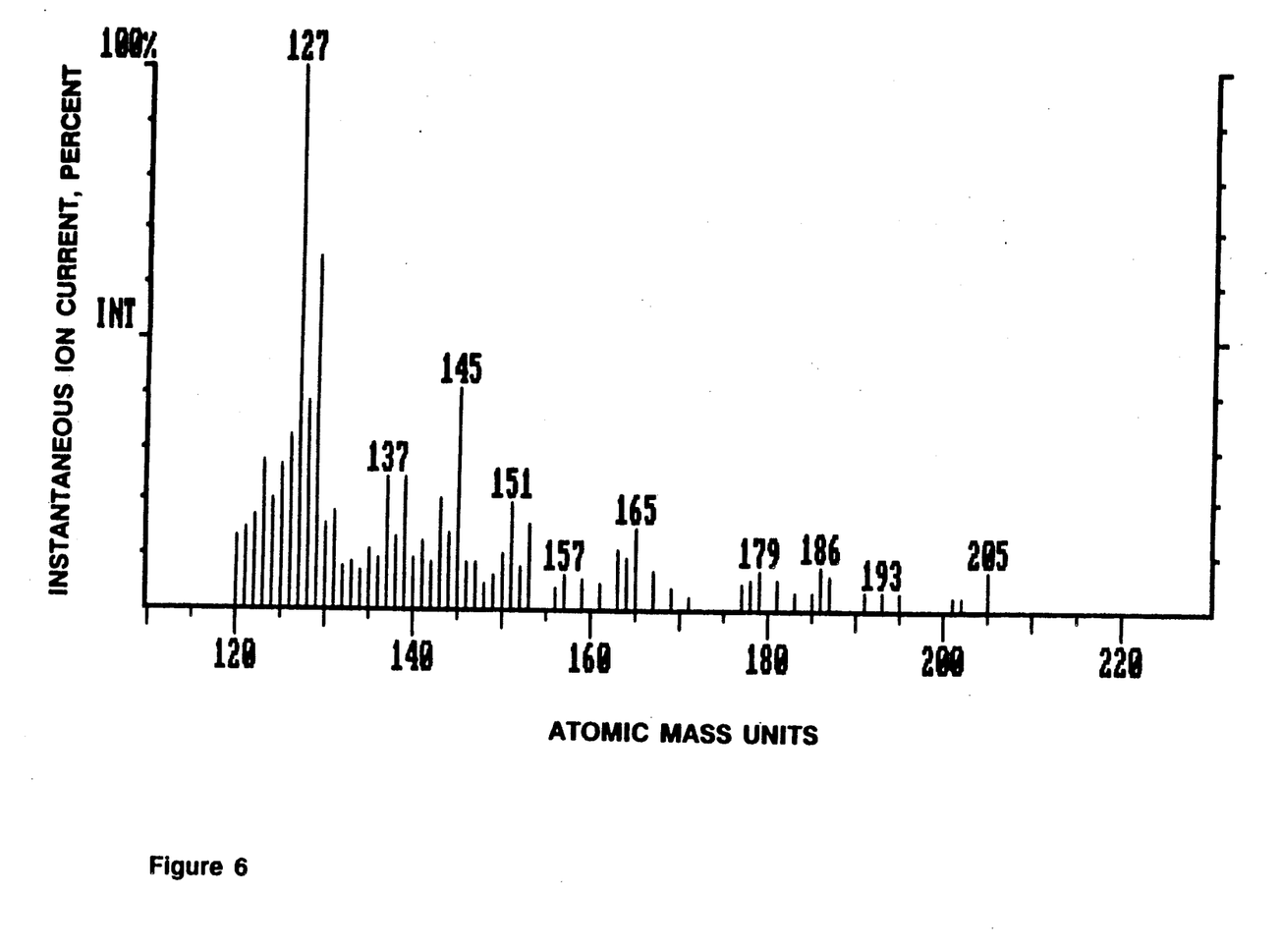
FIG. 6 is a record at the peak of evolution from the pyrolysis of red oak pulp of Kappa number equal to 84.9 where the cellulose lines dominate at 127 and 145 mass units and the remaining lines from lignin are significant.

Another sample spectrum of a red oak pulp sample of Kappa number equal to 84.9 is shown in FIG. 6. In this case, strong peaks from cellulose at 127 and 145 as well as small lignin peaks at the mass numbers observed in previous figures are observed.

Figure 7:
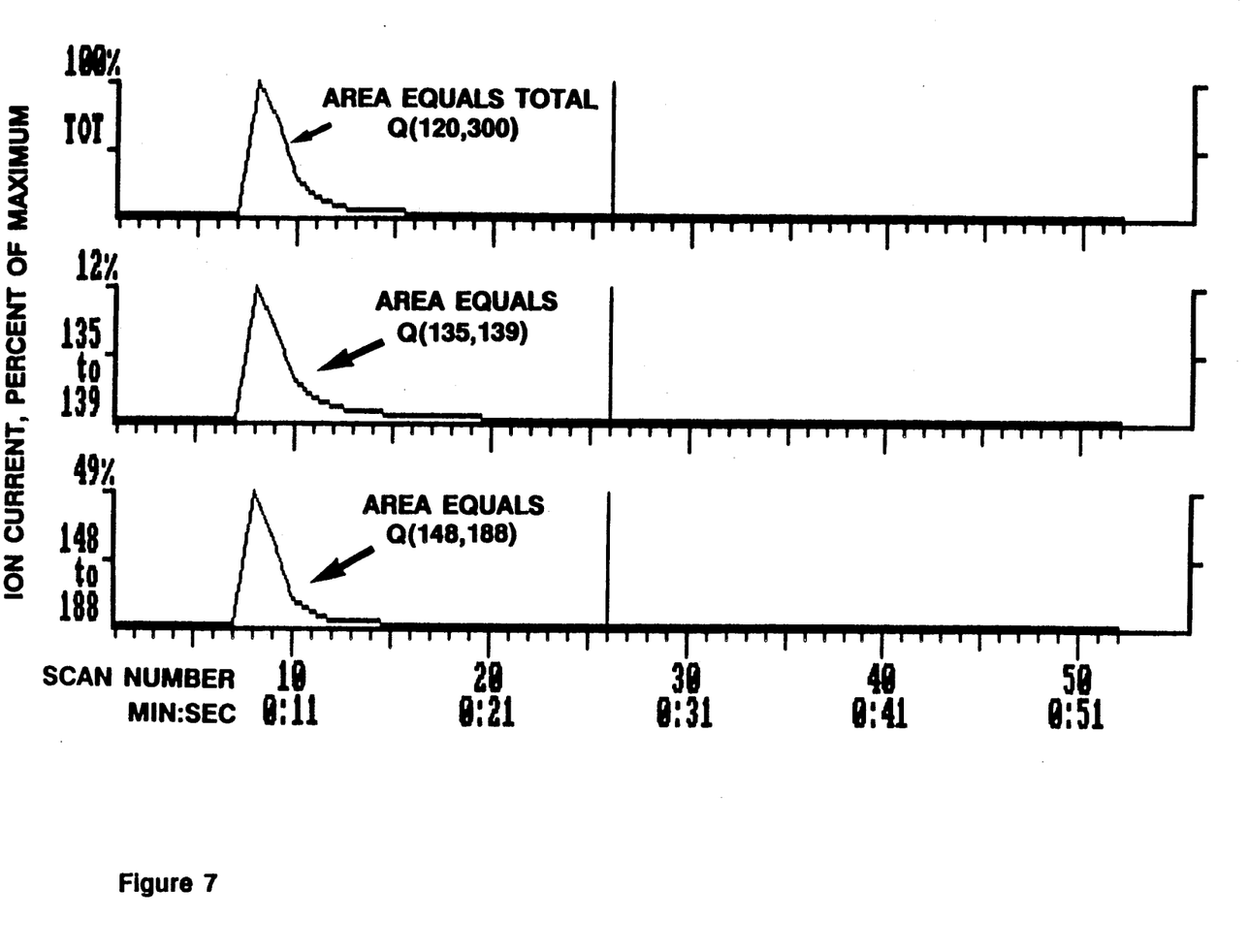
FIG. 7 is a record of pyrolysis profiles of pine chips over a duration of 60 seconds, of the total ion current, of the lignin peak in the group 135 to 139 mass units and of the total of many lines from lignin in the range 148 to 188 where pine wood has major lines.

Before quantitative determinations are made, the ion currents must be integrated. In FIG. 7, the total ion currents during a pyrolysis scan of pine wood are shown. The total ion current refers to all the masses in the range 120 to 300 atomic mass units. For the first 6 seconds after start, there are no products in this mass range. The pyrolysis button is pressed at the end of 6 seconds. The ion current rises rapidly to a maximum (where 100% means 575,020 counts) and then decreases because of dilution by hydrogen. By about 20 seconds, the total ion current is practically near zero. The second profile represents the ion current from the lignin peak at 137 atomic mass units. Because each line has sidebands associated with it, it has been found desirable to include 2 mass units on either side and consider line group such as 137±2 for quantitative evaluation. This profile is very similar to the first one. The maximum value in this lignin peak is 12% of 575,020 counts. The third profile, which has the same shape, represents the ion currents from 148 to 188 which include all the lignin peaks of pine wood. The peak is now 49% of the total ion current in the mass range 120 to 300.

Because the shapes of these are similar, it is clear that this method of continuous dilution by hydrogen is very regular. Pyrolysis products of different mass numbers behave similarly and no products condense out. (If the pyrolysis chamber is not heated, condensation occurs and large differences in pyrolysis can be observed).

The areas under these profiles are determined. For example, the quantity Q (135, 139) represents the charge detected in the range 135 to 139 atomic mass units which is the area under the second profile in FIG. 7.

Quantitative Determination

The charge ratios of products from lignin to those from all products from lignin and cellulose is defined by [Q(135, 139)+Q(148, 188)]÷Q(120, 300). The three ratios are the three areas in FIG. 7. Several samples of pulp from red oak and loblolly pine wood were pyrolyzed at 550° C. and analyzed in the above manner. These were samples for which both Kappa number and Klason lignin number had been determined by chemical analyses. The two numbers were linearly related and obeyed the relation.

*Kappa number=7.47+607.3 (Klason lignin)*

Figure 8:
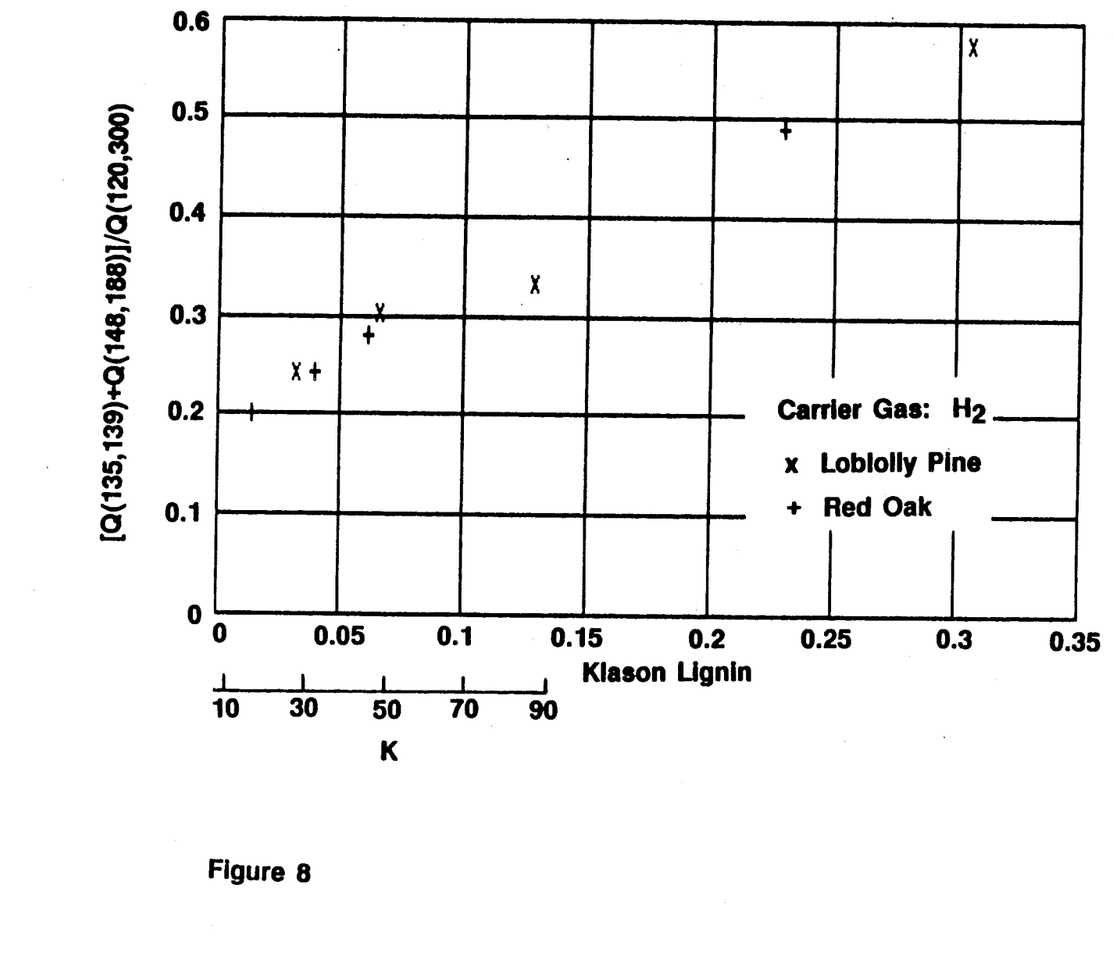
FIG. 8 is plot of the Q ratio (which measures the total ion charge due to several lines from lignin compared to the total ion charge from all components) vs. lignin content, either as Klason lignin or as Kappa numbers, the data being obtained from known samples of pine and red oak pulp.

The Q ratio is shown plotted vs. both Kappa number and Klason lignin in FIG. 8. It is seen that results for red oak pulps, red oak chips, pine pulp and pine wood fall on the same straight line. To achieve this correlation, peaks in red oak spectra beyond 188 had to be deliberately suppressed. The correlation using only those peaks seen in the pyrolysis products of pine wood is successful in producing a simple linear relation between the Q ratio and lignin content as determined by the Kappa number or Klason lignin.

Figure 9:
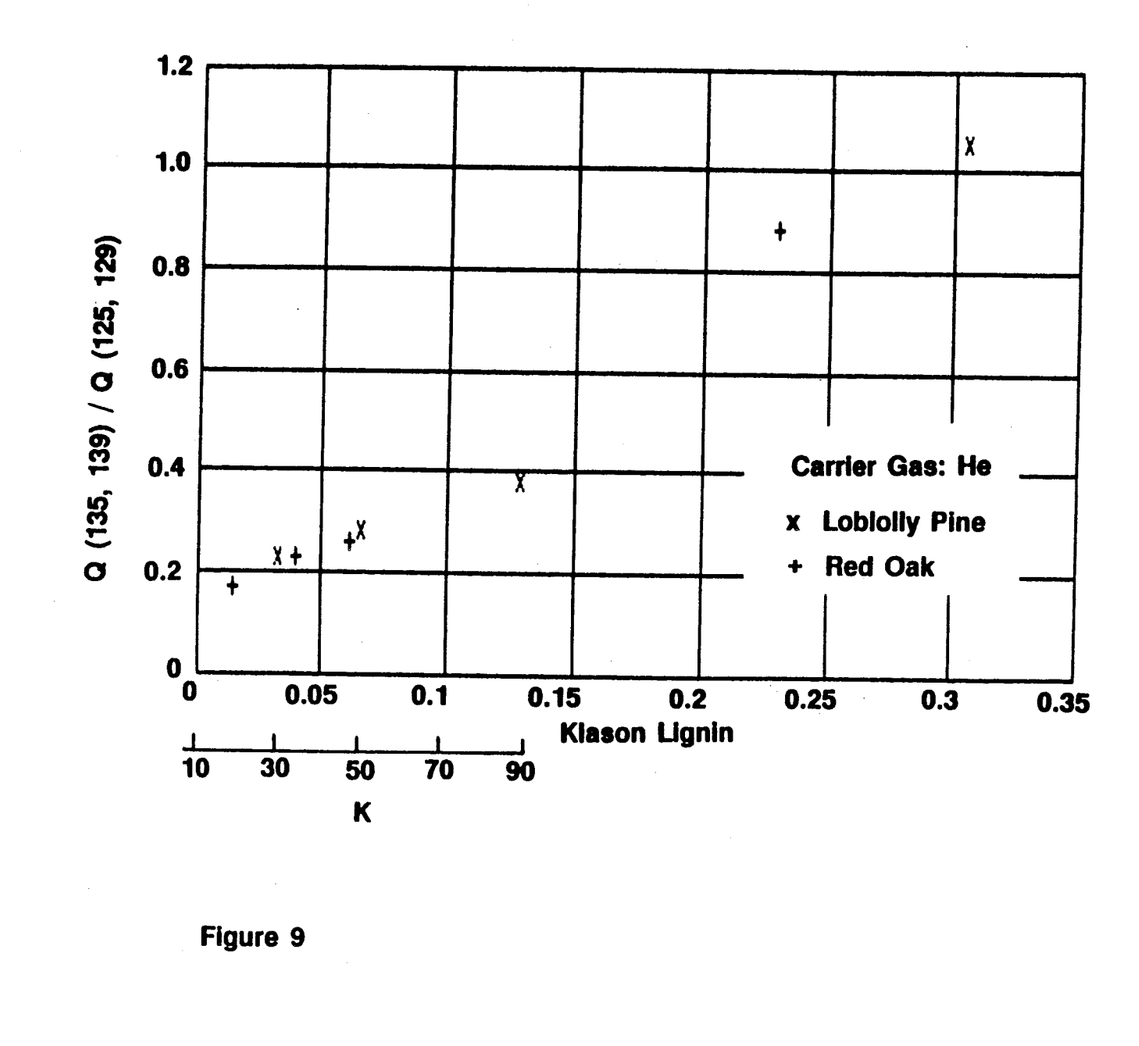
FIG. 9 is a plot of a Q ratio formed from one lignin group at 137+2 mass units to one cellulose group at 127+2 atomic mass units using helium as the pyrolysis gas.

When pyrolysis is conducted in an inert atmosphere of helium using it as the carrier gas, correlations of Q ratios defined above were not as simple as in hydrogen. Instead a simpler ratio relating one lignin group to one cellulose group was successful. The ratio Q(135, 139)/Q(125, 129) is shown plotted vs. lignin content in FIG. 9.

Reproducibility tests using multiple samples from the same pulp sample of Kappa 45.1 showed that the derived pyrolysis Kappa number was 45.1±0.71, where the variance is 0.71. Chemical Kappa numbers in the TAPPI method are repeatable to 0.2 Kappa below Kappa 20 and are repeatable to 1.2% between 20 and 190. For example at Kappa 45, TAPPI tests are claimed to repeat to 0.54.

Pyrolysis Temperature

Figure 10:
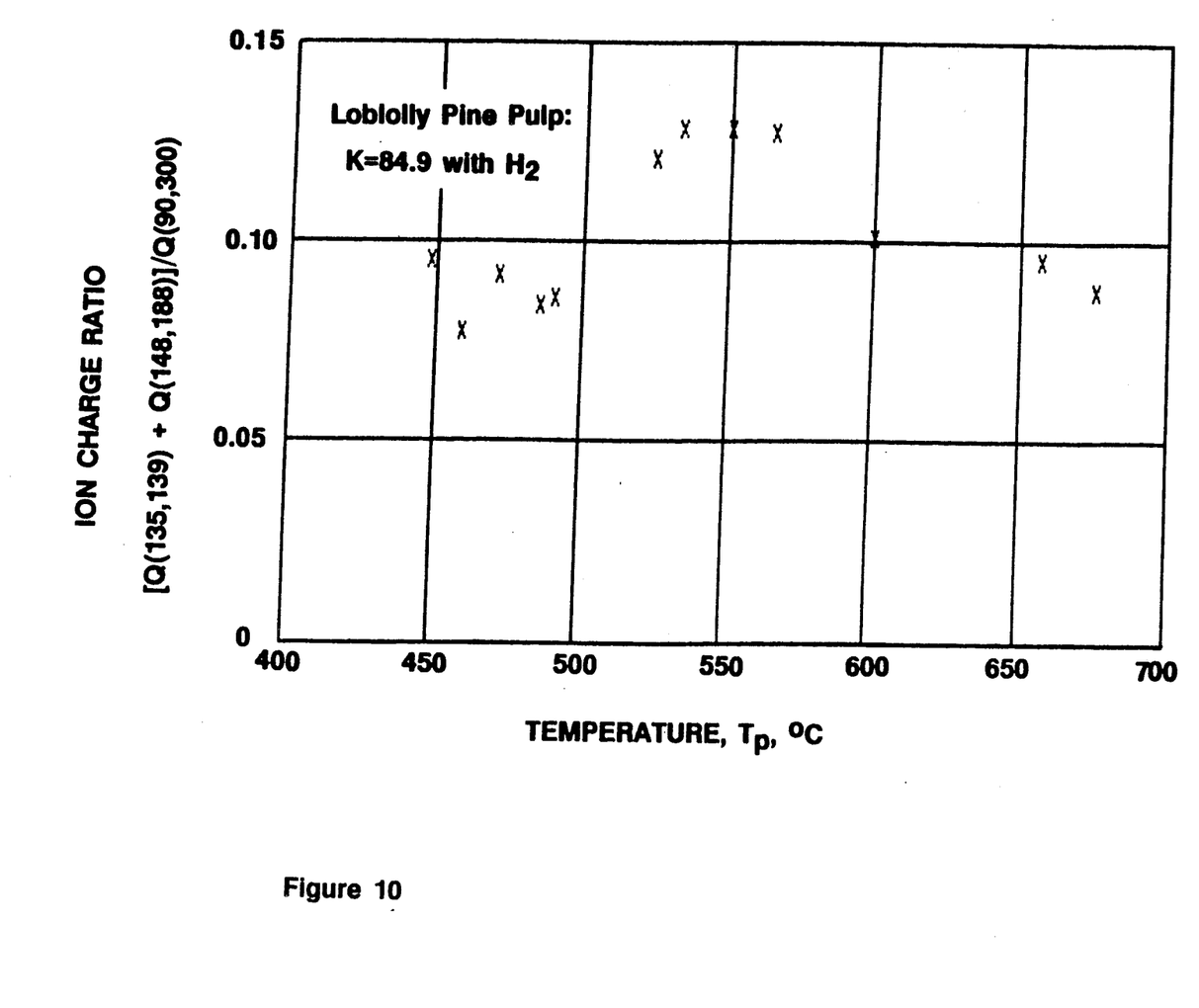
FIG. 10 is a plot of the Q ratio vs. pyrolysis temperature indicating that the best temperature for lignin measurement is at the peak of evolution which occurs at 550° C.

For a sample of pine pulp of Kappa number 84.9, data were acquired over a range of temperatures from 440° C. to 680° C. The Q ratio varies with temperature as shown in FIG. 10. It is seen that 550° C. is the temperature at which Q is a maximum. Above this temperature, pyrolysis products break down further and below this temperature, pyrolysis is incomplete. Variations of ±20° C. around 550° C. are tolerable and the present simple pyrolyzer with a fixed heating current pulse is adequate to produce reproducible results.

Conclusion

Pyrolysis in a hydrogen atmosphere at 550° C. is suitable for producing mass spectra for quantitative determination of lignin content. Samples of a few milligram are adequate to determine the Kappa number with a standard deviation comparable to that in the TAPPI method. The Q ratio is linearly related to lignin content over the whole range from cellulose to bare wood and the relation is the same for woods as different as pine and red oak. Pyrolysis in helium is also possible using a different Q ratio.

REFERENCES

1. Kappa number of pulp—Document T236 hm-85 copyright 1984 TAPPI.
2. STFI OPTI-Kappa, Asea Master Pulp & Paper brochure
3. R. Evans et al., "Direct Mass-Spectrometric Studies of the Pyrolysis of Carbonaceous Fuels. III Primary Pyrolysis of Lignin," Journal of Analytical and Applied Pyrolysis 9 (1986), pg. 207-236.

The embodiments of the invention in which an exclusive property or privilege is claimed are defined as follows:

1. A method of rapid measurement, accurate to plus or minus two percent, of the lignin content of a small sample of lignocellulosic matter such as paper, pulp or black liquor comprising the steps of:
   (a) constructing a compact pyrolysis chamber, electrically heated to temperatures near 120° C. to prevent condensation of gaseous products of pyrolysis,
   (b) constructing a small cup of chemically inert metal such as platinum welded to a ribbon of poorly heat conducting metal such as stainless steel, which can be heated electrically by a prescribed short duration pulse of electrical current to enable rapid pyrolysis of said sample at a predetermined temperature,
   (c) placing said sample in said pyrolysis cup, allowing a hydrogen carrier gas to enter and displace air in said pyrolysis chamber, without mixing, such that the environment for pyrolysis which is reducing or inert is achieved in a short time,
   (e) allowing said prescribed pulse of current to heat and pyrolize said sample under optimum conditions of product gas evolution to achieve a reproducible temperature profile with the optimum (maximum) temperature for lignin being 550° C.±20° C.,
   (f) allowing continuous and smooth dilution by said carrier gas during sampling of said gaseous products for mass spectral analysis by a mass spectrometer or species separation by a gas chromatograph,
   (g) using controlled electrical heating means to prevent condensation of gases in the transfer capillary lines of stainless steel or quartz by heating to approximately 200° C.,
   (h) sampling a small part of said products on the order of 1 part in 500 by three flow dividing capillaries, thereby avoiding the use of flow control valves, the use of which is detrimental to reproducible operation,
   (i) determining the ion currents at different masses in the range 120 to 300 atomic mass units, over the whole interval during pyrolysis and dilution, typically of duration 60 seconds,
   (j) integrating said ion currents to yield collected charges over said interval,
   (k) calculating charges Q(135, 139) in the mass range 135 to 139 a.m.u. plus charges Q(148, 188) in the mass range 148 to 188 a.m.u. which represents the contribution from lignin,
   (l) dividing the quantity in (j) by the total change Q(120, 300) in the mass range 120 to 300 a.m.u. characteristic of both cellulose and lignin, to get a Q ratio which is proportional to the lignin content of said sample over a wide range 0 to 35%,
   (m) alternately, in the case of helium as a carrier gas, deriving the ratio Q(135, 139)/Q(125, 129) derived from a single mass group of lignin and a single mass group of cellulose,
   (n) using a sample of filter paper of zero Kappa number and a standard pulp of known Kappa number to establish the calibration between said Q ratios and Kappa number,
   (o) in the case of gas chromatographic analysis, determining appropriate areas corresponding to the products from lignin and cellulose to determine the equivalents of said Q ratios.

* * * * *